United States Patent [19]

Kristinsson et al.

[11] Patent Number: 4,521,597

[45] Date of Patent: Jun. 4, 1985

[54] PROCESS FOR PRODUCING SULFONYLUREAS HAVING A HERBICIDAL ACTION

[75] Inventors: Haukur Kristinsson, Bottmingen; Werner Töpfl, Dornach, both of Switzerland

[73] Assignee: Ciba Geigy Corporation, Ardsley, N.Y.

[21] Appl. No.: 542,312

[22] Filed: Oct. 14, 1983

[30] Foreign Application Priority Data

Oct. 25, 1982 [CH] Switzerland .................. 6202/82

[51] Int. Cl.³ .................. C07D 251/18; C07D 251/46; C07D 251/52; C07D 239/69
[52] U.S. Cl. .................................... 544/3; 544/211; 544/212; 544/206; 544/207; 544/208; 544/209; 544/113; 544/122; 544/123; 544/96; 544/63; 544/60; 544/55; 544/320; 544/321; 544/324; 544/331; 544/323; 544/330; 544/332
[58] Field of Search ................ 544/211, 212, 208, 209, 544/123, 96, 55, 320, 331, 323, 332, 206, 207, 113, 122, 63, 60, 321, 324; 21/206, 207, 113, 122, 63, 60, 321, 324, 3, 330

[56] References Cited

U.S. PATENT DOCUMENTS 4,301,286 11/1981 Schwing et al. .................. 544/211
4,302,241 11/1981 Levitt .................................... 71/92

FOREIGN PATENT DOCUMENTS 0023422 2/1981 European Pat. Off. .
0024215 2/1981 European Pat. Off. .
0044807 1/1982 European Pat. Off. .
0044808 1/1982 European Pat. Off. .
2715786 10/1977 Fed. Rep. of Germany .

OTHER PUBLICATIONS

Sandmeyer, "Ueber Derivative der Kohlensäure Chlorimidokohlensäureäthylester", Ber. 19, 862 (1886).
Auwers et al., "Ueber Symmetrische αα-Dimethylglutarsäuren", Ann 287, 310-311, (1895).
Meyer, "Oxygen-to-Nitrogen Rearrangement of Diethyl N-(p-Tolylsulfonyl) . . . ", J. Org. Chem. 28, 2902-2903, (1963).
Höth et al., "Organylsilyl-borane", Chem. Ber. 99, 2197-2205, (1966).

Primary Examiner—John M. Ford
Attorney, Agent, or Firm—Edward McC. Roberts; Fredrick H. Rabin

[57] ABSTRACT

A novel process for producing sulfonylureas of the formula I having a herbicidal action and an action regulating plant growth

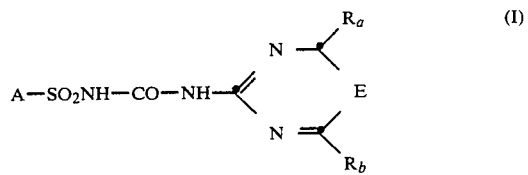

wherein A is an unsubstituted or substituted phenyl, naphthyl, furan, thiophene or pyridine group, E is a nitrogen atom or the methine group, $R_a$ is hydrogen, halogen, $C_1$-$C_5$-alkyl, $C_1$-$C_5$-haloalkyl, $C_1$-$C_5$-alkoxy, $C_1$-$C_5$-haloalkoxy, $C_1$-$C_5$-alkylthio or $C_2$-$C_{10}$-alkoxyalkoxy, and $R_b$ is the same as $R_a$ or is an unsubstituted or substituted amino group, and salts thereof, which process comprises firstly condensing an imidocarbonic acid ester with a sulfonyl chloride of the formula II to the sulfonylimidocarbonic acid diester of the formula IV

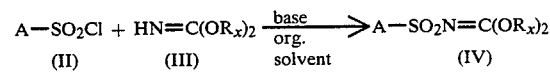

wherein R is an alkyl group, and reacting this in an ethereal solvent in the presence of sodium hydride or potassium tertbutylate with a 2-aminopyrimidine or 2-amino-1,3,5-triazine of the formula V, and finally reacting the formed sulfonylisourea of the formula VI in an organic solvent with hydrochloric acid to obtain the sulfonylurea of the formula I, and isolating this as such or as a salt;

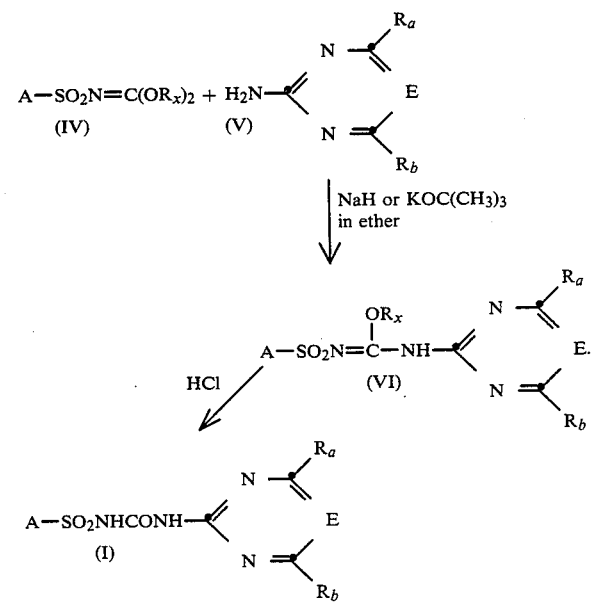

The sulfonylimidocarbonic acid diesters of the formula IV and certain sulfonylisoureas of the formula VI, required as intermediates, are novel compounds. The process has the advantage that no sulfonamides are needed as intermediate.

5 Claims, No Drawings

PROCESS FOR PRODUCING SULFONYLUREAS HAVING A HERBICIDAL ACTION

The present invention relates to a novel process for producing sulfonylureas having a herbicidal action and an action regulating plant growth, and also to novel sulfonylimido carbonic acid esters and N-sulfonyl-N'-triazinyl- or pyrimidinylisoureas produced as intermediates.

The sulfonylureas correspond to the general formula I

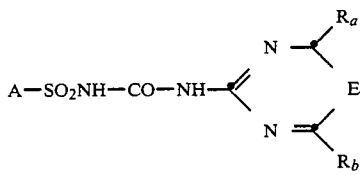

wherein
A is a radical of the formula

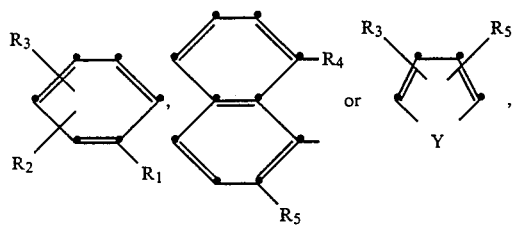

Y is oxygen, sulfur or

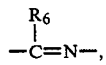

$R_1$ is hydrogen, halogen, nitro, trifluoromethyl, $C_1$-$C_5$-alkyl, $C_1$-$C_5$-alkoxy, —$COR_7$, —$S(O)_m C_1$-$C_5$-alkyl, —$SO_2R_{10}$, $XR_{11}$ or —$OSO_2 C_1$-$C_5$-alkyl, $R_2$ is hydrogen, fluorine, chlorine, bromine, nitro, $C_1$-$C_5$-alkyl, $C_1$-$C_5$-alkoxy, trifluoromethyl, $C_1$-$C_5$-haloalkoxy or —$COR_7$, $R_3$ is hydrogen, fluorine, chlorine, bromine, nitro, methoxy or trifluoromethyl, $R_4$ is hydrogen, halogen, nitro, $C_1$-$C_5$-alkyl, methoxy, —$COR_7$ or —$SO_2NR_8R_9$, $R_5$ is hydrogen, fluorine, chlorine, bromine, nitro, $C_1$-$C_5$-alkyl, $C_1$-$C_5$-alkoxy, trifluoromethyl, —$S(O)_m$-$C_1$-$C_5$-alkyl, —$COR_7$ or —$SO_2NR_8R_9$, $R_6$ is hydrogen, fluorine, methyl or methoxy, $R_7$ is hydrogen, $C_1$-$C_5$-alkyl, $C_1$-$C_5$-haloalkyl, $C_1$-$C_5$-alkoxy, $C_1$-$C_5$-haloalkoxy, $C_2$-$C_{10}$-alkoxyalkoxy, $C_3$-$C_5$-alkenyloxy, $C_3$-$C_5$-alkenyloxy, phenoxy, benzyloxy, $C_1$-$C_5$-alkylthio or —$NR_8R_9$, $R_8$ is hydrogen, $C_1$-$C_5$-alkyl, cyanoalkyl having a maximum of 5 carbon atoms, methoxy, ethoxy or $C_3$-$C_5$-alkenyl, $R_9$ is hydrogen, $C_1$-$C_5$-alkyl or $C_3$-$C_5$-alkenyl, or $R_8$ and $R_9$ together with the nitrogen atom binding them form a 5- or 6-membered, saturated heterocycle which can contain an oxygen or sulfur atom as ring member, $R_{10}$ is $C_1$-$C_5$-haloalkoxy or —$NR_8R_9$, $R_{11}$ is $C_1$-$C_5$-alkyl which is substituted by halogen, $C_1$-$C_5$-alkoxy, —$S(O)_m C_1$-$C_5$-alkyl, —$S(O)_m C_1$-$C_5$-haloalkyl or $C_2$-$C_5$-alkenyl which can be substituted by one of the stated radicals, X is oxygen or —$S(O)_m$—, m is zero, one or two, E is the methine group or nitrogen, $R_a$ is hydrogen, halogen, $C_1$-$C_5$-alkyl, $C_1$-$C_5$-haloalkyl, $C_1$-$C_5$-alkoxy, $C_1$-$C_5$-haloalkoxy, $C_1$-$C_5$-alkylthio, $C_2$-$C_{10}$-alkoxyalkyl or $C_2$-$C_{10}$-alkoxyalkoxy, $R_b$ is the same as $R_a$ or is an amino group

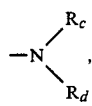

wherein
$R_c$ is hydrogen, methyl or ethyl, and
$R_d$ is hydrogen, methyl, ethyl or methoxy,
and also the salts of these compounds are included.

By halogen is meant within the scope of the above definition in general: fluorine, chlorine, bromine or iodine, fluorine and chlorine being preferred.

Examples of alkyl are: methyl, ethyl, n-propyl, i-propyl or the isomeric butyl groups. Alkyl itself is to be understood as being a substituent or a part of another substituent, for example alkoxy or alkylthio. Preferred alkyl groups are in each case unbranched alkyl chains, especially however methyl and ethyl.

By alkenyl is meant as a rule: allyl, 2-butenyl, 3-butenyl, 2-isobutenyl, isopropenyl, 2-pentenyl, 3-pentenyl and 4-pentenyl, particularly allyl and 4-pentenyl.

By alkynyl is meant in general: propargyl, 2-butynyl, 3-butynyl, methylpropargyl, 2-pentynyl, 3-pentynyl and 4-pentynyl.

The heterocycles which are covered by the definition of the radical A are: thiophene, furan and pyridine.

The sulfonylureas to be produced by the novel process according to the invention are described, together with their properties, for example in the U.S. Pat. Nos. 4,301,286 and 4,302,241, in the published European Patent Applications Nos. 23422, 44807 and 44808 or in the German Offenlegungsschrift No. 2,715,786.

These sulfonylureas have hitherto been produced either by reaction of a corresponding sulfonylisocyanate with an appropriate amine, or by reaction of a sulfonylamide with a carbamic acid ester derived from the respective amine to be used, especially a phenylcarbamate.

The known processes are disadvantageous in that the reaction has to be performed either with isocyanate derivatives or with isothiocyanate derivatives, the handling of which is difficult on account of the high reactivity of this class of compounds; or in that in the synthesis from phenylcarbamates ecologically unfavourable by-products, for example phenols, are formed. In addition, a number of ortho-substituted arylsulfonylamides are difficult to produce or cannot be produced. In the process of the present invention sulfonamides are not needed as intermediates.

It is hence the object of the present invention to provide a process which avoids the use of compounds difficult to handle or difficult to produce, and which also avoids the occurrence of by-products damaging to the environment.

It is suggested according to the invention that the sulfonylureas corresponding to the formula I which have a herbicidal action and an action regulating plant growth be produced by a novel process.

The process according to the invention proceeds in several stages. In the first stage, a sulfonyl chloride of the formula II $$A-SO_2Cl \qquad (II),$$

wherein A has the meaning defined above, is condensed in an inert phase system or solvent, in the presence of at least the equimolar amount of a base as acid-binding agent and at a temperature of between 0° and 100° C., with an imidocarbonic acid ester of the formula III

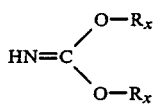
(III)

in which $R_x$ is $C_1-C_5$-alkyl, to form a sulfonylimidocarbonic acid diester of the formula IV

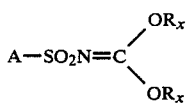
(IV)

in which A and $R_x$ have the meanings defined above.

The imidocarbonic acid esters of the formula III are known: cp. for example Liebigs Ann. Chem. 287, 310 (1895) and Chem. Ber. 19, 862 (1886).

Some N-benzenesulfonylimido-carbonic acid esters corresponding to the formula IV (those wherein A is the phenyl, para-tolyl or para-chlorophenyl group) are known and were produced from the corresponding benzenesulfonylamide (cp. Arch. Pharmaz. 300 (1967) 553; J. Org. Chem. 28 (1963) 2902 and Chem. Ber. 99 (1966) 2200).

The synthesis procedure according to the invention is novel and renders possible the production of sulfonylimido-carbonic acid esters of the formula IV directly from the sulfonyl chloride, with by-passing of the sulfonamide. The sulfonylimido-carbonic acid esters of the formula IV according to the invention are novel compounds.

Suitable solvents for this process stage are hydrocarbons, such as benzene, toluene and xylene; ethers, such as diethyl ether, ethylene glycol dimethyl ether, diethylene glycol dimethyl ether, tetrahydrofuran and dioxane; ketones, such as acetone, ethyl methyl ketone and cyclohexanone; nitriles, such as acetonitrile and propionitrile; and dimethyl sulfoxide. The reaction is performed in the presence of at least equimolar amounts of a base, or in an at least molar excess of the imino derivative to be used. Suitable bases are carbonates, such as sodium and potassium carbonate, hydrogen carbonates, such as sodium and potassium hydrogen carbonate, oxides, such as calcium and magnesium oxide, and tertiary amines, such as trimethylamine, triethylamine, quinuclidine, quinoline, pyridine and tripropylamine. The base is advantageously used in excess. There are thus preferably used 1 to 5 mols of base, especially 1.1 to 1.5 mols, per mol of sulfonyl chloride. Larger excesses of base are used in particular when the reaction is performed without solvent, and the base, preferably a liquid tertiary amine, serves simultaneously as the reaction medium. The reaction temperatures are between 0° and 100° C., preferably between 10° and 80° C.

In the second stage of the process, the sulfonylimidocarbonic acid diester of the formula IV, obtained from the first stage, is reacted in an inert solvent in the presence of a strong base, at a temperature of between 0° and 100° C., with a 2-aminopyrimidine or a 2-amino-1,3,5-triazine of the formula V

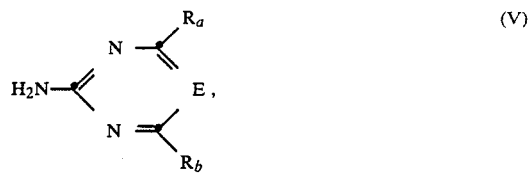
(V)

wherein E, $R_a$ and $R_b$ have the meanings defined above, to form a sulfonylisourea.

The reaction of the N-para-tolylsulfonylimido-carbonic acid diethyl ester with pyrrolidine and n-butylamine is described in J. Org. Chem. 28 (1963) 2902.

The solvent used for this process stage is selected for example from the group comprising: diethyl ether, dipropyl ether, dioxane, tetrahydrofuran, ethylene glycol dimethyl ether and diethylene glycol dimethyl ether. The strong bases used are alkali metal hydrides, alkali metal alcoholates or alkali metal alkylates, for example sodium hydride or potassium tert-butylate.

In the final stage, the sulfonylisourea of the formula VI obtained in the second stage

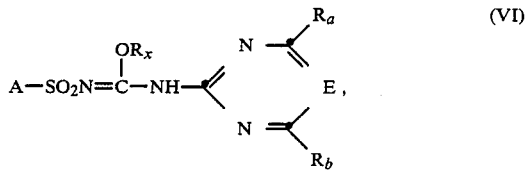
(VI)

wherein A, E, $R_a$, $R_b$ and $R_x$ have the meanings defined above, is reacted in an organic solvent, in the presence of a hydrogen halide and at a temperature of 0°–100° C., to give the sulfonylurea of the formula I, and this urea is then isolated as such or as a salt.

Suitable hydrogen halides are particularly hydrogen chloride and hydrogen bromide. Isoureas of the formula VI are known from the European Patent Application No. 24 215. They are produced by alkylation of the corresponding sulfonylureas, or they can be produced also according to the following reaction scheme:

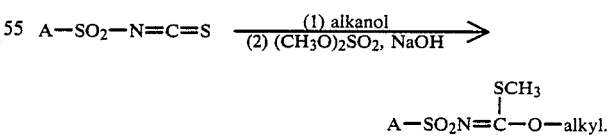

A sulfonylisothiocyanate obtained by reaction of sulfonamide with carbon disulfide is reacted firstly with an alkanol, and then with dimethyl sulfate and sodium hydroxide solution to obtain the thiomethyl-sulfonylimido-carbonic acid ester, which is subsequently reacted with sulfonyl chloride to the sulfonylimido-carbonic acid ester-monochloride, and further with the lithium salt of an amine to give the isourea:

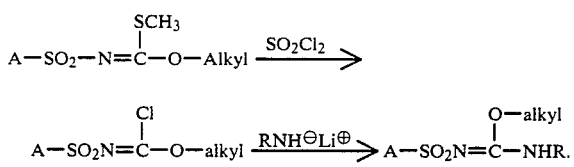

On account of its dependence on sulfonamides as starting material and on account of its complicated nature, this synthesis procedure for the production of isoureas is not easy to carry out. Furthermore, the methylthio chloride formed in the process is undesirable for ecological reasons.

A preferred embodiment of the process according to the invention comprises reacting a sulfonyl chloride of the formula II with the imidocarbonic acid diethyl ester in the presence of a tertiary amine in an organic solvent, isolating the resulting sulfonylimidocarbonic acid ester of the formula IV by concentrating the mother liquor by evaporation, and, if necessary, purifying the product by chromatography through a silica gel column, and then reacting the product, in an ethereal solvent in the presence of sodium hydride or potassium tert-butylate, with a 2-aminotriazinyl or 2-aminopyrimidine of the formula V, isolating the sulfonylisourea of the formula VI by concentration by evaporation, and washing the residue with dilute acid, then reacting it further as crude product, by heating in an organic solvent, with hydrochloric acid at 50° C. to give the sulfonylurea of the formula I, and isolating this as such or as a salt. The hydrochloric acid can be used, depending on whether the solvent is miscible with water or not, as an aqueous solution or in the gaseous form.

The starting compounds of the formula II are known and can be produced by known methods.

The sulfonylimidocarbonic acid diesters of the formula IV as well as certain isoureas of the formula VI are novel and were developed specifically for carrying out the process according to the invention. They therefore form further subject matter of the present invention.

The novel sulfonylimido-carbonic acid diesters correspond to the formula IV

wherein A has the meaning defined under the formula I, $R_1$ must not however be hydrogen, and $R_x$ is $C_1$–$C_5$-alkyl.

Also novel are those sulfonylisoureas of the formula VIa

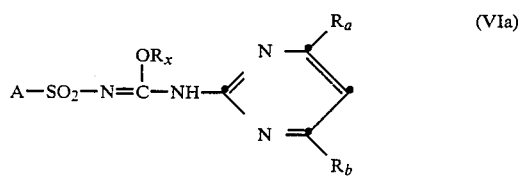

wherein $R_a$ is the difluoromethoxy radical, whilst A, $R_b$ and $R_x$ have the meanings defined above; as well as the phenylsulfonylisoureas of the formula VIII

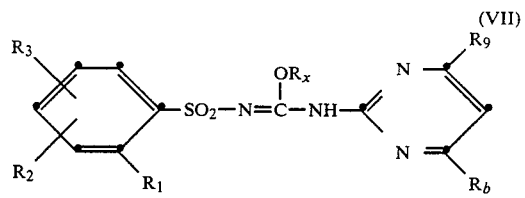

wherein $R_1$ is a group —$XR_{11}$, and $R_2$, $R_3$, $R_a$, $R_b$, $R_x$ and E have the meanings defined above.

The following Examples serve to further illustrate the invention.

EXAMPLE 1

Production of N-(2-difluoromethoxybenzenesulfonyl)-imidocarbonic acid diethyl ester

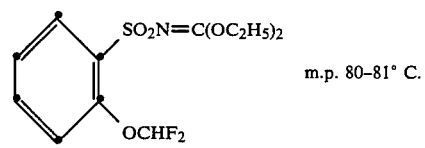

m.p. 80–81° C.

11.1 g (0.11 mol) of triethylamine are added dropwise at room temperature, with stirring, to a solution of 24.3 g (0.1 mol) of 2-difluoromethoxy-benzenesulfonyl chloride and 11.7 g (0.1 mol) of imidocarbonic acid diethyl ester in 70 ml of acetone. The reaction proceeds slightly exothermically. The reaction mixture is stirred for some hours at room temperature, and the triethylamine hydrochloride is then filtered off. The mother liquor is concentrated by evaporation, and the oil remaining is chromatographed by means of chloroform/ether/petroleum ether (3:3:2) on a silica gel column. After the eluate has been evaporated, there remain 23 g of the above ester, which crystallise (72% of theory), m.p. 80°–81° C.

Analysis: calculated: C 44.58%, H 4.68%, N 4.33%, S 9.92%, F 11.75%; found: C 44.5%, H 4.6%, N 4.3%, S 10%, F 11.9%.

The following benzenesulfonyl-imidocarbonic acid esters are obtained in a manner analogous to that described in Example 1:

TABLE 1

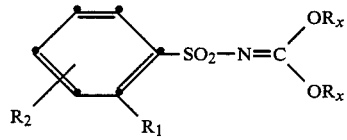

| $R_1$ | $R_2$ | $R_x$ | Physical data |
|---|---|---|---|
| —COOCH$_3$ | H | C$_2$H$_5$ | m.p.: 92–94° C. |
| —COOCH$_3$ | H | CH$_3$ | |
| —COOCH$_3$ | H | C$_4$H$_9$ | |
| —Cl | H | C$_2$H$_5$ | m.p.: 73–75° C. |
| —Cl | H | CH$_3$ | |
| —Cl | H | C$_6$H$_{13}$ | |
| —COOC$_2$H$_5$ | H | C$_2$H$_5$ | |
| —CONH$_2$ | H | C$_2$H$_5$ | |
| —CONHCH$_3$ | H | C$_2$H$_5$ | |
| —CON(CH$_3$)$_2$ | H | C$_2$H$_5$ | |
| —COH | H | C$_2$H$_5$ | |
| —COCH$_3$ | H | C$_2$H$_5$ | |
| —F | H | C$_2$H$_5$ | |
| —Br | H | C$_2$H$_5$ | |

TABLE 1-continued

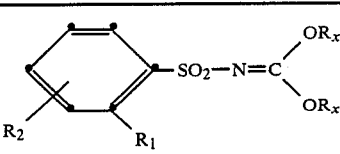

| R₁ | R₂ | Rₓ | Physical data |
|---|---|---|---|
| —C≡N | H | C₂H₅ | m.p.: 78–80° C. |
| —NO₂ | H | CH₃ | |
| —NO₂ | H | C₂H₅ | |
| —CF₃ | H | C₂H₅ | |
| —CH₃ | H | C₂H₅ | |
| —OCH₃ | H | C₂H₅ | |
| —SCH₃ | H | C₂H₅ | |
| —SO₂CH₃ | H | C₂H₅ | |
| —SOCH₃ | H | C₂H₅ | |
| —SO₂CH(CH₃)₂ | H | C₂H₅ | |
| —SO₂C₃H₇—n | H | C₂H₅ | |
| —SO₂N(CH₃)₂ | H | C₂H₅ | |
| —OCHF₂ | H | CH₃ | |
| —OCHF₂ | H | C₂H₅ | m.p.: 80–81° C. |
| —OCF₃ | H | C₂H₅ | |
| —OC₂F₅ | H | C₂H₅ | |
| —OCF₂CHF₂ | H | C₂H₅ | |
| —OCH₂CH₂OCH₂ | H | C₂H₅ | |
| —OCH₂CH₂Cl | H | C₂H₅ | |
| —OCCl=CHCl | H | C₂H₅ | |
| —OCH₂CH=CH₂ | H | C₂H₅ | |
| —OCH₂C≡CH | H | C₂H₅ | |
| —SCHF₂ | H | C₂H₅ | m.p. 72–74° C. |
| —OCHF₂ | 5-OCHF₂ | C₂H₅ | |
| —Cl | 6-Cl | C₂H₅ | |
| —OCH₃ | 5-OCH₃ | C₂H₅ | |
| —OCHF₂ | 6-Cl | C₂H₅ | |

TABLE 2

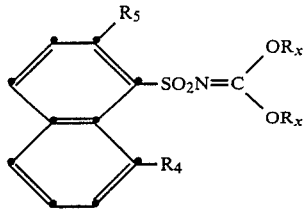

| R₁ | Rₓ | Y | Position of the sulfonyl group | Physical data |
|---|---|---|---|---|
| 2-COOCH₃ | C₂H₅ | S | 3 | |
| 3-COOCH₂ | C₂H₅ | S | 2 | |
| 4-COOCH₃ | C₂H₅ | S | 3 | |
| 2-NO₂ | C₂H₅ | S | 3 | |
| 3-NO₂ | C₂H₅ | S | 2 | |
| 2-Cl | C₂H₅ | S | 3 | |
| 3-Cl | C₂H₅ | S | 2 | |
| 2-SO₂N(CH₃)₂ | C₂H₅ | S | 3 | |
| 3-SO₂N(CH₃)₂ | C₂H₅ | S | 2 | |
| 2-SO₂CH₃ | C₂H₅ | S | 3 | |
| 3-SO₂CH₃ | C₂H₅ | S | 2 | |
| H | C₂H₅ | O | 2 | |
| H | C₂H₅ | C=N | 2 | |
| 2-Cl | C₂H₅ | C=N | 3 | |
| 2-OCH₃ | C₂H₅ | C=N | 3 | |
| 2-F | C₂H₅ | C=N | 3 | |
| 2-SO₂CH₃ | C₂H₅ | C=N | 3 | |

TABLE 3

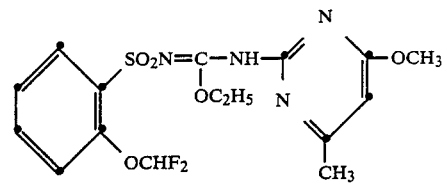

| R₄ | R₅ | Rₓ | Physical data |
|---|---|---|---|
| H | H | C₂H₅ | |
| Cl | H | C₂H₅ | |
| Cl | Cl | C₂H₅ | |
| CH₃ | H | C₂H₅ | |
| CH₃ | Cl | C₂H₅ | |
| OCH₃ | CH₃ | C₂H₅ | |

EXAMPLE 2

Production of N-(2-difluoromethoxy-benzenesulfonyl)-N'-(4-methoxy-6-methylpyrimidin-2-yl)-O-ethyl-isourea

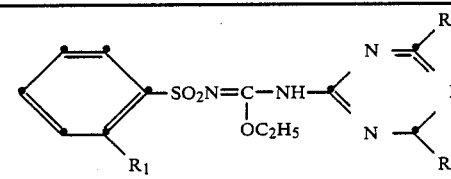

To a solution of 11.2 g (0.1 mol) of potassium tert-butylate in 125 ml of tetrahydrofuran are added at room temperature, with stirring, 13.9 g (0.1 mol) of 2-amino-4-methoxy-6-methylpyridimine. Stirring is maintained for 2 hours at room temperature, and 32.3 g (0.1 mol) of N-(2-difluoromethoxy-benzenesulfonyl)-imido carbonic acid diethyl ester (obtained according to Example 1) are then added, the reaction mixture being stirred for a further 20 hours. The mixture is subsequently concentrated by evaporation, and the residue is taken up in water and rendered acid with hydrochloric acid. The acid solution is extracted with ethyl acetate; the organic phases are then collected, dried, and concentrated by evaporation to leave a solid residue, which is suspended in ether and again filtered off. The yield is 34.5 g (83% of theory) of the above sulfonylisourea, m.p. 131°–133° C.

Analysis: calculated: C 46.15%, H 4.36%, N 13.46%, S 7.70%, F 9.13%; found: C 46.4%, H 4.4%, N 13.4%, S 7.7%, F 9.2%.

The following isoureas are produced in a manner analogous to that of this Example:

TABLE 4

| R₁ | Rₐ | R_b | E | Physical data |
|---|---|---|---|---|
| —COOCH₃ | —OCHF₂ | —CH₃ | CH | |
| —COOCH₃ | —OCHF₂ | —OCH₃ | CH | |

TABLE 4-continued

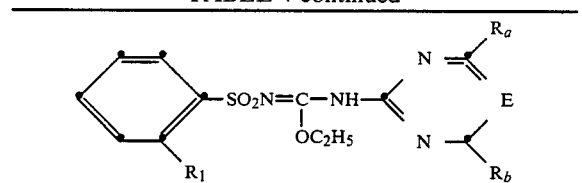

| $R_1$ | $R_a$ | $R_b$ | E | Physical data |
|---|---|---|---|---|
| —COOCH₃ | —OCHF₂ | —Cl | CH | |
| —COOCH₂ | —OCHF₂ | —N(CH₃)₂ | CH | |
| —COOCH₃ | —OCHF₂ | —OCHF₂ | CH | |
| —COOCH₃ | —OCHF₂ | —CF₃ | CH | |
| —OCHF₂ | —CH₃ | —OCH₃ | N | |
| —OCHF₂ | —OCH₃ | —OCH₃ | N | m.p.: 83–87° C. |
| —OCHF₂ | —CH₃ | —CH₃ | CH | m.p.: 112–114° C. |
| —OCHF₂ | —CH₃ | —OCH₃ | CH | m.p.: 131–133° C. |
| —OCHF₂ | —OCHF₂ | —CH₃ | CH | |
| —OCHF₂ | —OCHF₂ | —OCH₃ | CH | |
| —OCH₂CH₂OCH₂ | —CH₃ | —OCH₃ | N | |
| —OCH₂CH₂OCH₃ | —OCH₃ | —OCH₃ | N | |
| —OCH₂CH₂OCH₂ | —CH₃ | —CH₃ | CH | |
| —OCH₂CH₂OCH₃ | —CH₃ | —OCH₃ | CH | |
| —OCH₂CH₂OCH₃ | —OCHF₂ | —CH₃ | CH | |
| —OCH₂CH₂OCH₃ | —OCHF₂ | —OCH₃ | CH | |
| —SCHF₂ | —CH₃ | —OCH₃ | N | |
| —SCHF₂ | —OCH₃ | —OCH₃ | N | |
| —SCHF₂ | —CH₃ | —CH₃ | CH | |
| —SCHF₂ | —CH₃ | —OCH₃ | CH | |
| —SCHF₂ | —OCHF₂ | —CH₃ | CH | |
| —SCHF₂ | —OCHF₂ | —OCH₃ | CH | |
| —OCH₂CH₂Cl | —CH₃ | —OCH₃ | N | |
| —OCH₂CH₂Cl | —OCH₃ | —OCH₃ | N | |
| —OCH₂CH₂Cl | —CH₃ | —CH₃ | CH | |
| —OCH₂CH₂Cl | —CH₃ | —OCH₃ | CH | |
| —OCH₂CH₂Cl | —OCHF₂ | —CH₃ | CH | |
| —OCH₂CH₂Cl | —OCHF₂ | —OCH₃ | CH | |
| —OCCl=CHCl | —CH₃ | —OCH₃ | N | |
| —OCCl=CHCl | —OCH₃ | —OCH₃ | N | |
| —OCCl=CHCl | —CH₃ | —CH₃ | CH | |
| —OCCl=CHCl | —CH₃ | —OCH₃ | CH | |
| —OCCl=CHCl | —OCHF₂ | —CH₃ | CH | |
| —OCCl=CHCl | —OCHF₂ | —OCH₃ | CH | |
| —OCH=CH₂ | —CH₃ | —OCH₃ | N | |
| —OCH=CH₂ | —OCH₃ | —OCH₃ | N | |
| —OCH=CH₂ | —CH₃ | —CH₃ | CH | |
| —OCH=CH₂ | —CH₃ | —OCH₃ | CH | |
| —OCH=CH₂ | —OCHF₂ | —CH₃ | CH | |
| —OCH=CH₂ | —OCHF₂ | —OCH₃ | CH | |
| —OCF₃ | —CH₃ | —OCH₃ | N | |
| —OCF₃ | —OCH₃ | —OCH₃ | N | |
| —OCF₃ | —CH₃ | —CH₃ | CH | |
| —OCF₃ | —CH₃ | —OCH₃ | CH | |
| —OCF₃ | —OCHF₂ | —CH₃ | CH | |
| —OCF₃ | —OCHF₂ | —OCH₃ | CH | |
| —OC₂F₅ | —CH₃ | —OCH₃ | N | |
| —OC₂F₅ | —OCH₃ | —OCH₃ | N | |
| —OC₂F₅ | —CH₃ | —CH₃ | CH | |
| —OC₂F₅ | —CH₃ | —OCH₃ | CH | |
| —OC₂F₅ | —OCHF₂ | —CH₃ | CH | |
| —OC₂F₅ | —OCHF₂ | —OCH₃ | CH | |
| —Cl | —OCHF₂ | —OCH₃ | CH | |
| —Cl | —OCHF₂ | —N(CH₃)₂ | CH | |
| —Cl | —OCHF₂ | —CH₃ | CH | |
| —COOCH₃ | —CH₃ | —CH₃ | CH | m.p.: 85–88° |
| —COOCH₃ | —CH₃ | —OCH₃ | CH | m.p.: 96–98° |
| —CONH | —OCHF₂ | —OCH₃ | CH | |
| —CONH₂ | —OCHF₂ | —N(CH₃)₂ | CH | |
| —CONH₂ | —OCHF₂ | —CH₃ | CH | |
| —CONHCH₃ | —OCHF₂ | —OCH₃ | CH | |
| —CONHCH₃ | —OCHF₂ | —N(CH₃)₂ | CH | |
| —CONHCH₃ | —OCHF₂ | —CH₃ | CH | |
| —CON(CH₃)₂ | —OCHF₂ | —OCH₃ | CH | |
| —CON(CH₃)₂ | —OCHF₂ | —N(CH₃)₂ | CH | |
| —CON(CH₃)₂ | —OCHF₂ | —CH₃ | CH | |

TABLE 4-continued

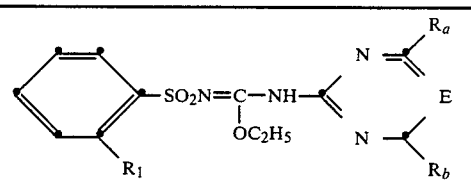

| $R_1$ | $R_a$ | $R_b$ | E | Physical data |
|---|---|---|---|---|
| —NO₂ | —OCHF₂ | —OCH₃ | CH | |
| —NO₂ | —OCHF₂ | —N(CH₃)₂ | CH | |
| —NO₂ | —OCHF₂ | —CH₃ | CH | |
| —CF₃ | —OCHF₂ | —OCH₃ | CH | |
| —CF₃ | —OCHF₂ | —N(CH₃)₂ | CH | |
| —CF₃ | —OCHF₂ | —CH₃ | CH | |
| —OCH₃ | —OCHF₂ | —OCH₃ | CH | |
| —OCH₃ | —OCHF₂ | —N(CH₃)₂ | CH | |
| —OCH₃ | —OCHF₂ | —CH₃ | CH | |
| —SCH₃ | —OCHF₂ | —OCH₃ | CH | |
| —SCH₃ | —OCHF₂ | —N(CH₃)₂ | CH | |
| —SCH₃ | —OCHF₂ | —CH₃ | CH | |
| —SC₃H₇—n | —OCHF₂ | —OCH₃ | CH | |
| —SC₃H₇—n | —OCHF₂ | —N(CH₃)₂ | CH | |
| —SC₃H₇—n | —OCHF₂ | —CH₃ | CH | |

EXAMPLE 3

Production of N-(2-difluoromethyl-benzenesulfonyl)-N'-(4,6-dimethyl-pyrimidin-2-yl)urea

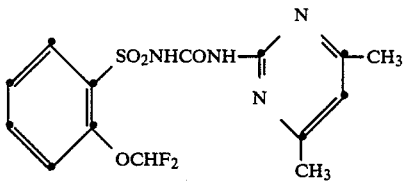

To a solution of 10 g of hydrogen chloride in 100 ml of dioxane are added at room temperature, with stirring, 8.0 g (0.02 mol) of N-(2-difluoromethoxybenzenesulfonyl)-N'-(4,6-dimethyl-pyrimidin-2-yl)-O-ethyl-isourea (obtained according to Example 2). The reaction mixture is then stirred at 50° C. for 12 hours, and subsequently concentrated by evaporation; the solid substance remaining is suspended in water and the suspension is filtered. The yield is 7.2 g (97% of theory) of the above urea, m.p. 190°–195° C.

Analysis: calculated: C 45.16%, H 3.79%, N 15.05%, S 8.61%, F 10.21%; found: C 44.8%, H 3.9%, N 15%, S 8.6%, F 10.2%.

The isoureas listed in Table 4 can be reacted in a manner according to that of the above Example.

What is claimed is:

1. A process for producing sulfonylureas which have a herbicidal action and an action regulating plant growth, and which correspond to the formula I

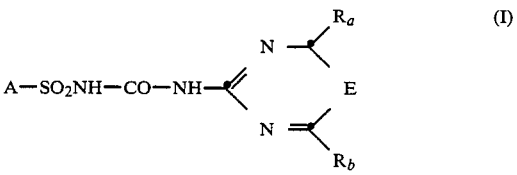

wherein

A is a radical of the formula

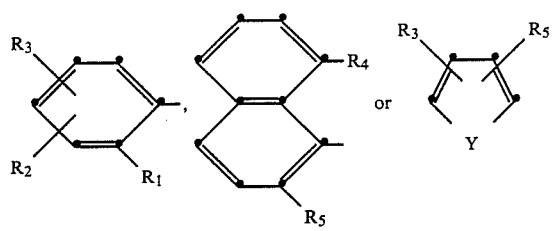

Y is oxygen, sulfur or

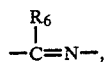

$R_1$ is hydrogen, halogen, nitro, trifluoromethyl, $C_1$-$C_5$-alkyl, $C_1$-$C_5$-alkoxy, —$COR_7$, —$S(O)_m$—$C_1$-$C_5$-alkyl, —$SO_2R_{10}$, $XR_{11}$ or —$OSO_2C_1$-$C_5$-alkyl, $R_2$ is hydrogen, fluorine, chlorine, bromine, nitro, $C_1$-$C_5$-alkyl, $C_1$-$C_5$-alkoxy, trifluoromethyl, $C_1$-$C_5$-haloalkoxy or —$COR_7$, $R_3$ is hydrogen, fluorine, chlorine, bromine, nitro, methoxy or trifluoromethyl, $R_4$ is hydrogen, halogen, nitro, $C_1$-$C_5$-alkyl, methoxy, —$COR_7$ or —$SO_2NR_8R_9$, $R_5$ is hydrogen, fluorine, chlorine, bromine, nitro, $C_1$-$C_5$-alkyl, $C_1$-$C_5$-alkoxy, trifluoromethyl, —$S(O)_mC_1$-$C_5$-alkyl, —$COR_7$ or —$SO_2NR_8R_9$, $R_6$ is hydrogen, fluorine, methyl or methoxy, $R_7$ is hydrogen, $C_1$-$C_5$-alkyl, $C_1$-$C_5$-haloalkyl, $C_1$-$C_5$-alkoxy, $C_1$-$C_5$-haloalkoxy, $C_2$-$C_{10}$-alkoxyalkoxy, $C_3$-$C_5$-alkenyloxy, $C_3$-$C_5$-alkynyloxy, phenoxy, benzyloxy, $C_1$-$C_5$-alkylthio or —$NR_8R_9$, $R_8$ is hydrogen, $C_1$-$C_5$-alkyl, cyanoalkyl having a maximum of 5 carbon atoms, methoxy, ethoxy or $C_3$-$C_5$-alkenyl, $R_9$ is hydrogen, $C_1$-$C_5$-alkyl or $C_3$-$C_5$-alkenyl, or $R_8$ and $R_9$ together with the nitrogen atom binding them form a 5- or 6-membered, saturated heterocycle which can contain an oxygen or sulfur atom as ring member, $R_{10}$ is $C_1$-$C_5$-haloalkoxy or —$NR_8R_9$, $R_{11}$ is $C_1$-$C_5$-alkyl which is substituted by halogen, $C_1$-$C_5$-alkoxy, —$S(O)_mC_1$-$C_5$-alkyl, —$S(O)_m$-$C_1$-$C_5$-haloalkyl or $C_2$-$C_5$-alkenyl which can be substituted by one of the above radicals, X is oxygen or —$S(O)_m$—, m is zero, one or two, E is the methine group or nitrogen, $R_a$ is hydrogen, halogen, $C_1$-$C_5$-alkyl, $C_1$-$C_5$-haloalkyl, $C_1$-$C_5$-alkoxy, $C_1$-$C_5$-haloalkoxy, $C_1$-$C_5$-alkylthio, $C_2$-$C_{10}$-alkoxyalkyl or $C_2$-$C_{10}$-alkoxyalkoxy, $R_b$ is the same as $R_a$ or is an amino group

wherein $R_c$ is hydrogen, methyl or ethyl, and $R_d$ is hydrogen, methyl, ethyl or methoxy, and also the salts of these compounds, which process comprises condensing a sulfonyl chloride of the formula II

A—$SO_2Cl$ (II), in an inert phase system or organic solvent, in the presence of at least the equimolar amount of a base as acid-binding agent and at a temperature of 0° to 100° C., with an imidocarbonic acid ester of the formula III

in which $R_x$ is $C_1$-$C_5$-alkyl; isolating the formed sulfonylimidocarbonic acid diester of the formula IV

reacting it then in an inert solvent in the presence of a strong base, at a temperature of between 0° and 100° C., with a 2-aminopyrimidine or 2-aminotriazine of the formula V

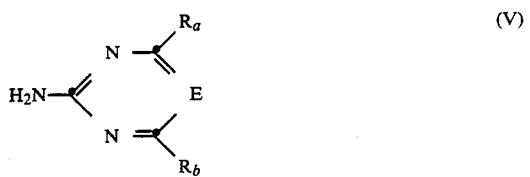

to give a sulfonylisourea of the formula VI

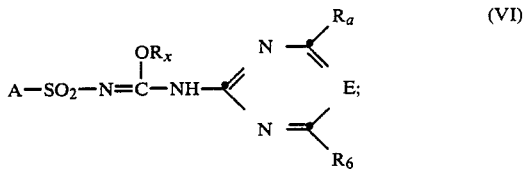

and subsequently converting this in the presence of a hydrogen halide in an inert solvent, at a temperature of 0°-100° C., into a sulfonylurea of the formula I; and finally isolating this as such or as a salt.

2. A process according to claim 1, which process comprises reacting a sulfonyl chloride of the formula II

A—$SO_2Cl$ (II), in an inert phase system or organic solvent, in the presence of a tertiary amine, with the imidocarbonic acid diethyl ester; reacting the resulting sulfonylimidocarbonic acid diester of the formula IV

in an anhydrous solvent, with sodium hydride or potassium tert-butylate and a 2-aminopyrimidine or 2-aminotriazine of the formula V

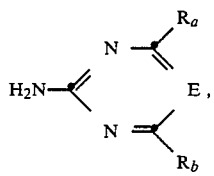

reacting the resulting sulfonylisourea of the formula VI

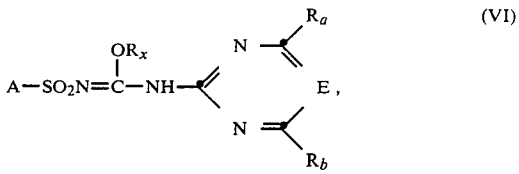

in an organic solvent with hydrochloric acid at 50° C. to obtain the sulfonylurea of the formula I; and isolating this as such or as a salt.

3. A process according to claims 1 or 2, wherein the reaction of the compounds II and III is performed in an inert phase mixture or organic solvent in the presence of triethylamine.

4. A process according to claims 1 or 2, wherein the reaction of the compounds IV and V is performed in an anhydrous solvent in the presence of potassium tert-butylate or sodium hydride.

5. A process according to claims 1 or 2, wherein the reaction of the sulfonylisourea of the formula VI with 10% hydrochloric acid is performed in a dioxane solution at 50° C.

* * * * *

UNITED STATES PATENT AND TRADEMARK OFFICE
CERTIFICATE OF CORRECTION

PATENT NO. : 4,521,597

DATED : June 4, 1985

INVENTOR(S) : Haukur Kristinnson and Werner Topfl

It is certified that error appears in the above-identified patent and that said Letters Patent is hereby corrected as shown below:

Claim 1, Column 10, Lines 60-67 should read--

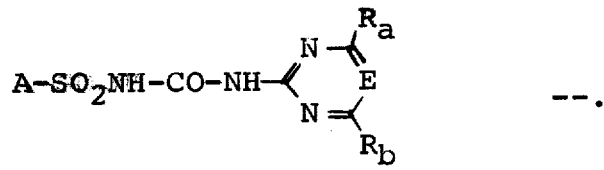

--.

Signed and Sealed this

Twenty-ninth Day of October 1985

[SEAL]

Attest:

DONALD J. QUIGG

Attesting Officer

Commissioner of Patents and
Trademarks—Designate